(12) United States Patent
Glyazer et al.

(10) Patent No.: US 10,161,660 B2
(45) Date of Patent: Dec. 25, 2018

(54) MEASUREMENT PATH OF A TEMPERATURE CONTROLLER FOR A THERMOELECTRIC MODULE

(71) Applicant: OBSHCHESTVO S OGRANICHENNOY OTVETSTVENNOSTYU "KOMPANIYA RMT", Nizhny Novgorod (RU)

(72) Inventors: Semen Aleksandrovich Glyazer, Moscow (RU); Gennady Gyusamovich Gromov, Moscow (RU); Aleksei Leonardovich Ogryzko, Moscow (RU)

(73) Assignee: OBSHCHESTVO S OGRANICHENNOY OTVETSTVENNOSTYU "KOMPANIYA RMT" (RU)

( * ) Notice: Subject to any disclaimer, the term of this patent is extended or adjusted under 35 U.S.C. 154(b) by 525 days.

(21) Appl. No.: 14/762,002

(22) PCT Filed: Sep. 19, 2013

(86) PCT No.: PCT/RU2013/000818
§ 371 (c)(1),
(2) Date: Jul. 20, 2015

(87) PCT Pub. No.: WO2014/062084
PCT Pub. Date: Apr. 24, 2014

(65) Prior Publication Data
US 2016/0010908 A1    Jan. 14, 2016

(30) Foreign Application Priority Data

Oct. 19, 2012 (RU) ................ 2012144547

(51) Int. Cl.
*F25B 49/00* (2006.01)
*G01N 27/20* (2006.01)
(Continued)

(52) U.S. Cl.
CPC .............. *F25B 49/00* (2013.01); *F25B 21/04* (2013.01); *F25B 49/005* (2013.01); *G01K 1/02* (2013.01);
(Continued)

(58) Field of Classification Search
None
See application file for complete search history.

(56) References Cited

U.S. PATENT DOCUMENTS 7,256,371 B2 * 8/2007 Crawford ............. H05B 1/0288
219/219
2007/0097718 A1 * 5/2007 Nahar ................... G01K 7/425
363/65

(Continued)

FOREIGN PATENT DOCUMENTS

RU       2274838 C1    4/2006
SU        515283 A    10/1976

(Continued)

OTHER PUBLICATIONS

International Search Report prepared by the Russian Patent Office dated Jan. 21, 2014, for International Application No. PCT/RU2013/000818.

*Primary Examiner* — Alexander Ghyka
(74) *Attorney, Agent, or Firm* — Sheridan Ross P.C.

(57) ABSTRACT

The device provides the possibility of feeding test signals to a thermoelectric module by virtue of the use of controllable switches and also makes it possible to increase test criteria and to detect faults and the causes of said faults at early stages outside of the use process of the thermoelectric (Continued)

module (TEM), as well as in periods between use. This technical result is achieved in that the device comprises a DC source, a measurement circuit, a first, a second, a third and a fourth controllable switch, which are used for feeding test signals and are switched on and off by a temperature controller. The first and the second controllable switches are used for connection to the DC source, and the third and fourth switches are grounded with the possibility of switching from the third controllable switch over to the first controllable switch and from the fourth controllable switch over to the second controllable switch. One of the conductors of the measurement circuit is connected between the first and the third controllable switches, and a second of the conductors is connected between the second and the fourth controllable switches. The conductors of the measurement circuit are intended for connection to the thermoelectric module and for transmitting measurement data to the temperature controller.

10 Claims, 2 Drawing Sheets

(51) Int. Cl.
| | | |
|---|---|---|
| | *G01K 15/00* | (2006.01) |
| | *G05D 23/24* | (2006.01) |
| | *G01K 1/02* | (2006.01) |
| | *F25B 21/04* | (2006.01) |
| | *G01N 25/72* | (2006.01) |

(52) U.S. Cl.
CPC ............ *G01K 15/00* (2013.01); *G01N 25/72* (2013.01); *G01N 27/20* (2013.01); *G05D 23/24* (2013.01)

(56) References Cited

U.S. PATENT DOCUMENTS

| | | | | |
|---|---|---|---|---|
| 2010/0150202 | A1* | 6/2010 | Asano | G01K 7/01 374/44 |
| 2011/0050141 | A1* | 3/2011 | Yeh | H02P 6/08 318/434 |
| 2011/0279074 | A1* | 11/2011 | Yeh | G01K 7/42 318/432 |
| 2012/0234022 | A1 | 9/2012 | Langsdorf | |
| 2013/0002358 | A1* | 1/2013 | Mitchell | G01D 3/036 330/289 |
| 2013/0322491 | A1* | 12/2013 | Gao | G01K 7/02 374/179 |
| 2014/0002050 | A1* | 1/2014 | Mitchell | G05F 3/242 323/311 |
| 2014/0132002 | A1* | 5/2014 | Watanabe | F02N 11/0866 290/31 |

FOREIGN PATENT DOCUMENTS

| | | |
|---|---|---|
| SU | 1471089 A1 | 4/1989 |
| UA | 98594 C2 | 5/2012 |

* cited by examiner

MEASUREMENT PATH OF A TEMPERATURE CONTROLLER FOR A THERMOELECTRIC MODULE

CROSS REFERENCE TO RELATED APPLICATIONS

This application is a national stage application under 35 U.S.C. 371 and claims the benefit of PCT Application No. PCT/RU2013/000818 having an international filing date of Sep. 19, 2013, which designated the United States, which PCT application claimed the benefit of Russian Patent Application No. 2012144547 filed Oct. 19, 2012, the disclosure of both the above-identified applications are incorporated herein by reference.

FIELD OF THE INVENTION

The present utility model relates to the field of electronics, in particular to structures of temperature controllers (thermoregulators) intended for controlling operation of thermoelectric modules, and may be used for testing condition and operability of thermoelectric nodules.

The proposed utility model may be used in structures comprising thermoelectric modules (TEM) serving as cooling or heating elements intended for cooling, heating and thermally stabilizing various devices.

DESCRIPTION OF PRIOR ART

A thermoelectric module is a highly reliable device having a long service life (tens of years). Owing to its high reliability and a long service life, it is used in many responsible and expensive applications where frequent maintenance is excluded. The TEM operability diagnostics is important for detecting degradation processes and assessing possibility of operation failures at early stages. Further, a change in a thermoelectric module parameter by as low as a few per cent during the operation process presents a serious signal of its operability degradation in many applications, e.g., in optoelectronic applications [Generic Reliability Assurance Requirements for Optoelectronic Devices Used in Telecommunications Equipment. Telcordia Technologies Generic Requirements GR-468-CORE. Issue 2, September 2004, 186 p.].

It is known from the art that a comparison of initial and subsequent values of measured parameters, which are memorized in a temperature controller, enable to monitor the TEM operability and diagnose unfavorable reasons causing operability failures [RU 2 285 980, C2].

Also, the art teaches designs of single-crystal integrated controllers for the MAX-1978 and MAX-1979 thermoelectric modules [http://www.maximintegrated.com/datasheet/index.mvp/id/3527].

The known designs of temperature controllers for thermoelectric modules ensure bidirectional control (two directions of control current for the cooling and heating modes) of a thermoelectric module. The control algorithms are realized, such as control algorithms of P-type (proportional), PI-type (proportionally integral), PD-type (proportionally differential), PID-type (proportionally integral differential), etc. Controllers are provided with algorithms of automatic adjustment of parameters for a selected control law. They have a number of circuit operability monitoring functions (monitoring of current or voltage), threshold value limitation functions (for temperature, power settings) and other control functions.

The proposed design of a thermoelectric controller is most close, as to its functions, to the design of the Series 800 Thermoelectric Cooler Controller for a thermoelectric module [http://www.zionscientific.com/senes800.html].

A drawback of the above temperature controllers for a thermoelectric module is that they do not have the function of diagnosing a controlled object as such, i.e., a thermoelectric module (TEM). The only diagnosis method is the monitoring of current and voltage in the thermoelectric module power circuit in the process of operation, which may be used for assessing solely the current TEM operability, e.g., open power circuit—the thermoelectric module is damaged, sharp changes in power current or voltage—failure in process. The known temperature controller designs do not enable to carry out early diagnosis of TEMs.

No essential features of the claimed measurement path of a temperature controller for a thermoelectric module have been identified during patent searches; therefore, the proposed device complies with the novelty criterion. The claimed device may be used both in known designs of temperature controllers after their modification by adding the measurement path, as described below, and in new designs.

SUMMARY OF THE INVENTION

The objective of the proposed utility model is to develop a temperature controller design that enables to improve testing quality as well as carry out operability diagnosis of a controllable thermoelectric module for the purpose of detecting possible failure types and their reasons at early stages.

The technical effect of the proposed utility model consists in providing the possibility of feeding test signal to a TEM by using controllable switches. Furthermore, the use of the utility model is aimed at increasing the number of testing criteria characterizing the TEM operability as well as at ensuring detection of failures and reasons thereof at early stages outside the TEM operation process as well as during intervals between operation periods.

In order to solve the stated objective and achieve the above technical effect, the measurement path of a temperature controller for a thermoelectric module comprises a power source, a measuring circuit that is made double-wire, the first, second, third, and fourth controllable switches being switched ON/OFF by a temperature controller, the first and second controllable switches being used for connecting to a DC source intended for feeding a test signal, and the third and fourth switches being made grounded and being used for feeding a test signal with the possibility of connecting the third controllable switch to the first controllable switch and the fourth controllable switch to the second controllable switch; one of the measuring circuit wires is connected between the first and third controllable switches, and the other wire is connected between the second and fourth controllable switches, the measuring circuit wires being intended for connection to a thermoelectric module and transmission of measurements to a temperature controller.

Additional embodiments of the design are possible, wherein it is reasonable that:
  in order to measure a thermoelectric module temperature the first, second, third, and fourth controllable switches are switched OFF;
  in order to measure a thermoelectric module resistance, the first and fourth controllable switches are ON, and the second and third controllable switches are OFF;

and, then, the second and third controllable switches are ON, and the first and fourth controllable switches are OFF to provide the possibility of setting a rate of pairwise switching ON/OFF the said controllable switches;

in order to measure a Q-factor and a time constant of a thermoelectric module, at first the first and fourth controllable switches are ON, and the second and third controllable switches are OFF; and then, in order to measure thermoelectric Q and a time constant of the thermoelectric module, the second and third controllable switches are ON, and the first and fourth controllable switches are OFF for averaging data in the temperature controller.

The technical effect of the proposed utility model is achieved by introducing a hardware measurement path into the controller and by providing the possibility of measuring the TEM key parameters, i.e., resistance in the AC mode, thermoelectric Q and a time constant.

Measurements may be taken before and after the TEM work cycle as well as within a specially set pause during operation.

The above-said advantages of the utility model as well as its peculiar features are explained with the use of its best embodiment taken with reference to the accompanying drawings.

BEST MODE FOR CARRYING OUT THE INVENTION

Figure 1:
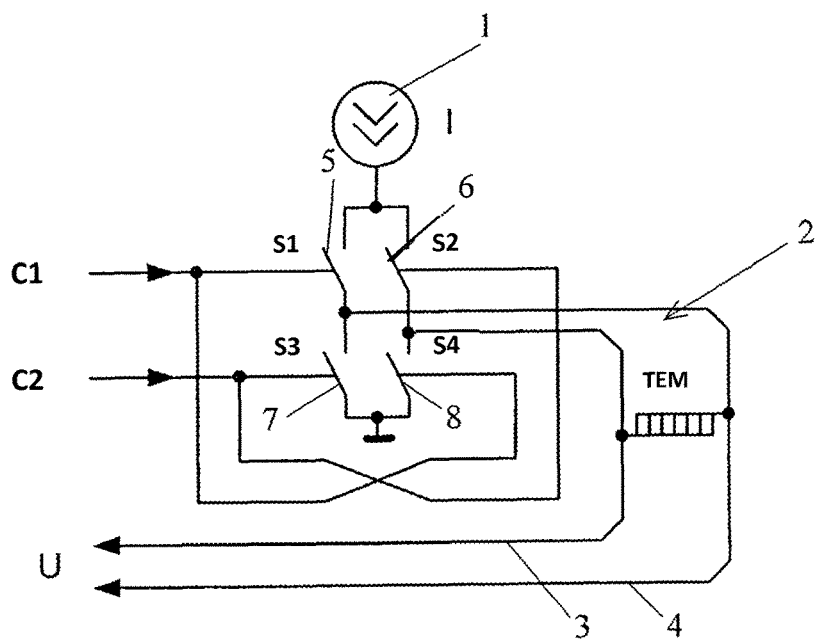
FIG. 1 shows the functional diagram of the claimed measurement path.

The measurement path of a temperature controller for a thermoelectric module (FIG. 1) comprises: a DC source 1, a double-wire measuring circuit 2 composed of wires 3 and 4. The first, second, third, and fourth controllable switches 5, 6, 7, 8, as used for feeding a test signal, are made switchable ON/OFF by a temperature controller. The first and second controllable switches 5, 6 are used for connection to the source 1, respectively, and are intended for feeding a test signal, and the third and fourth switches 7, 8 are made grounded and are provided with the possibility of connecting the third controllable switch 7 to the first controllable switch 5 and the fourth controllable switch 8 to the second controllable switch 6. One wire 3 of the measuring circuit 2 is connected between the first controllable switch 5 and the third controllable switch 7, and the second wire 4 is connected between the second controllable switch 6 and the fourth controllable switch 8. The wires 3 and 4 of the measuring circuit 2 are intended for connection to a thermoelectric module (TEM) and transmission of measurements to a temperature controller.

Figure 2:
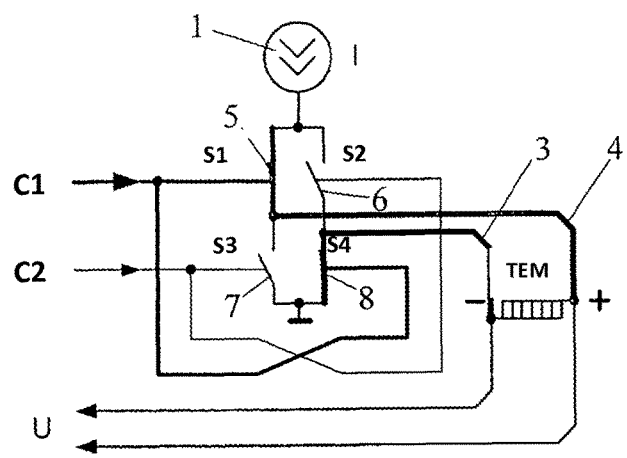
FIG. 2—same as in FIG. 1, when forming positive polarity voltage (provisionally)
Figure 3:
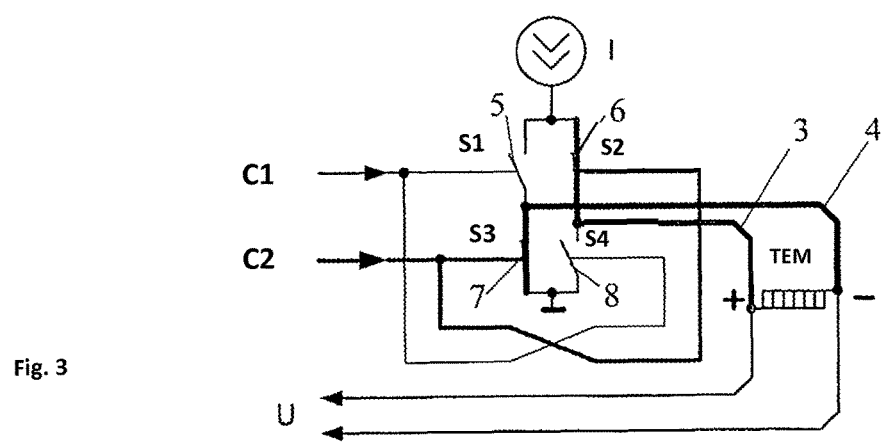
FIG. 3—same as in FIG. 1, when forming negative polarity voltage (provisionally)

The following designations are used in FIGS. 1-3: S1 . . . S4—controllable switches 5-8; C1, C2—control signals for the controllable switches 5, 6, 7, 8; I—DC source 1; TEM—thermoelectric module; U—voltage drop on a thermoelectric module to be transmitted to a temperature controller.

In order to measure a temperature of a thermoelectric module, the first, second, third, fourth controllable switches 5,6,7, 8 are OFF (FIG. 1).

In order to measure resistance of a thermoelectric module, the first and fourth controllable switches 5 and 8 are ON, and second and third controllable switches 6 and 7 are OFF (FIG. 2). Then, the second and third controllable switches 6 and 7 are ON, and the first and fourth controllable switches 5 and 8 are OFF (FIG. 3). The control signals C1 and C2 perform pairwise switching of the said controllable switches 5, 8 and 6, 7 with a set rate.

In order to measure a thermoelectric Q and a time constant of a thermoelectric module, at the beginning the first and fourth controllable switches 5 and 8 are ON, and the second and third controllable switches 6, 7 are OFF (FIG. 2). Then, in order to measure thermoelectric Q and a time constant of a thermoelectric module, the second and third controllable switches 6 and 7 are ON, and the first and fourth controllable switches 5 and 8 are OFF for averaging data on a thermoelectric Q and a time constant by a temperature controller.

The device works as follows (FIGS. 1-3).

The claimed measurement path enables to control, by means of control signals C1 and C2 generated by the controller microprocessor, controllable switches 5-8 (electronic, S1-S4) that ensure formation of a given polarity for a testing current (supplied from the source 1 of direct current I) fed to a TEM. The controller microprocessor measures a TEM voltage converted by an ADC.

In the diagram (FIG. 1) control signals C1, C2 fed to the controllable switches 5, 6, 7, 8 (S1 . . . S4) are absent, and the thermoelectric module is disconnected from the source 1 of direct current I.

FIGS. 2, 3 show how TEM voltage of positive or negative polarity is formed when the 4 switches (S1S4 and S2S3) present in this diagram are switched pairwise.

In one case (FIG. 2) the first and fourth controllable switches 5, 8 (S1 and S4) are ON and the second and third controllable switches 6, 7 (S2 and S3) are OFF, and the TEM voltage polarity, as shown in FIG. 2 is "plus" on the right. In another case (FIG. 3) the status of the control signals is changed—the first and fourth controllable switches 5, 8 (S1 and S4) are OFF, and the second and third controllable switches 6, 7 (S2 and S3) are ON—"plus" on the left.

When these switches are switched ON/OFF pairwise with a given rate, alternating current is supplied to a thermoelectric module because it is necessary for measuring resistance during TEM diagnosis.

A thermoelectric module may be diagnosed with the use of the proposed measurement path as follows.

Before starting the thermoelectric module operation, during a special time interval between its starts, or in the end of a work cycle the temperature controller performs the parameter diagnosis algorithm for a thermoelectric module, thus measuring the key parameters of the thermoelectric module according to the methods described below.

Temperature Measurement

No control signals are fed to the switches S1 . . . S4 from the controller microprocessor, and the thermoelectric module is disconnected from the source of current I (FIG. 1).

A temperature sensor, as included into the temperature controller (TC), measures a temperature of the thermoelectric module cold side or temperature of an object fixed to the cold side of the thermoelectric module, depending on the design of a controllable thermoelectric module with a cooling/thermal stabilization object. Since these measurements are taken while a thermoelectric module is OFF, this is an ambient temperature $T_a$.

Measurement of Resistance R of a Thermoelectric Module

The true resistance of a thermoelectric module is resistance measured with alternating current. In order to create such resistance, the first and fourth controllable switches 5 and 8 (S1S4) and the second and third controllable switches 6 and 7 (S2S3) are switched ON/OFF pairwise in accordance with FIGS. 2 and 3.

Resistance R is determined by measuring ohmic voltage $U_R$ on a thermoelectric module in the absence of thermal e.m.f. and any significant overheating of a thermoelectric module. For this, alternating-direction current I' of a small amplitude (~30 mA), as set by the source 1 of direct current (I), is fed to a thermoelectric module by switching the controllable switches 5-8 pairwise with a given rate. The typical frequency of the alternating current generated is 1 kHz.

The controller microprocessor calculates resistance as:

$$R = \frac{U_R}{I'} \quad (1)$$

Resistance thus obtained (resistance at alternating current) is memorized by the temperature controller.

A break in the TEM electric circuit—a module is damaged—may be diagnosed at the stage of measuring R. Apart from this, a deviation of a resistance R value from initial values during the operation process may indicate degradation of a thermoelectric module. If no break in the electric circuit is found, then the next measuring step may be fulfilled.

Measurement of the Thermoelectric Q-Factor Z

Direct electric current $I_Z$ of a small magnitude and one of possible polarities is fed to a thermoelectric module (FIG. 2), so that a steady-state temperature difference on the module is small (~2-4 degrees Centigrade). For this, a current value is set by the source 1 of direct current in the measurement path (FIG. 2) so as it is significantly lower than the certified value of maximum current $I_{max}$ for the thermoelectric module. For example, the current value should be set at the level of $I_Z=0.1-5\%$ of $I_{max}$.

Figure 5:
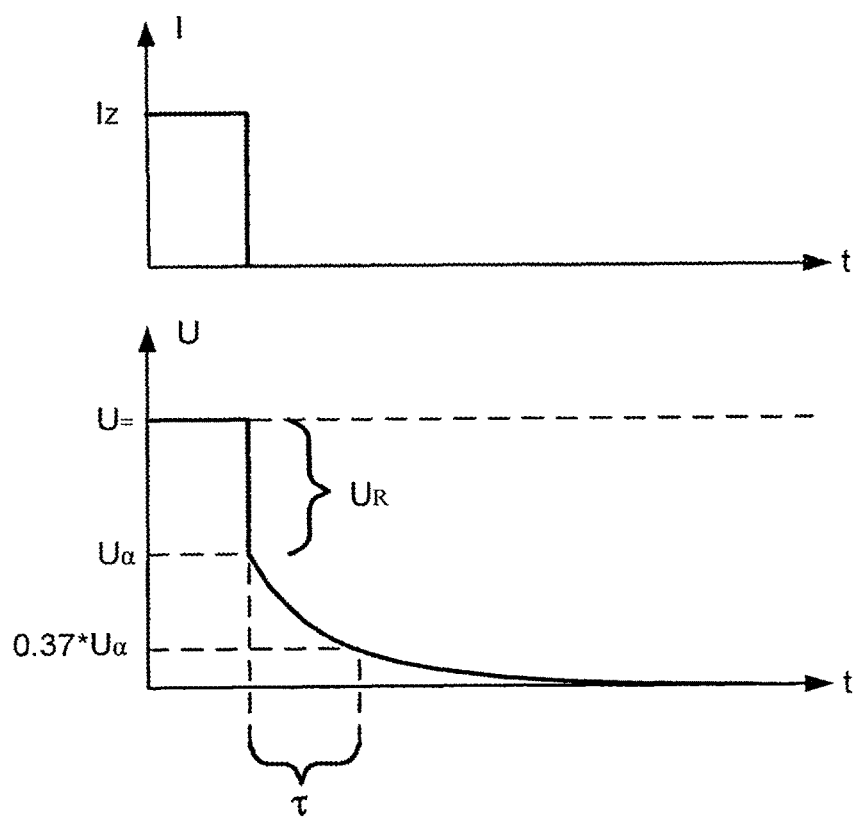
FIG. 5 shows a change in a time constant.

The controller measures a voltage magnitude on the thermoelectric module after voltage reaches a stationary level (FIG. 5).

This stationary voltage U is the sum of two values:

$$U_\Sigma = U_\alpha + U_R \quad (2)$$

where:
$U_\Sigma$ is value of stationary voltage measured;
$U_\alpha$ is thermal e.m.f. of the thermoelectric module, as arises due to the Seebeck effect;
UR is ohmic voltage drop that is determined by a value of passing current $I_Z$ and by resistance R of the thermoelectric module, as measured earlier.

$$U_\alpha = U_\Sigma - U_R = U_\Sigma - I_Z \times R \quad (3)$$

At this step a $U_\alpha$ value of thermal e.m.f. is calculated.

And the unknown thermoelectric Q-factor Z is calculated by the microprocessor of the temperature controller according to the following formula:

$$Z = (U_\alpha/U_R)/T_a \quad (4)$$

In order to improve measurement accuracy, thermoelectric Q is measured when the testing current of both polarities is fed to a thermoelectric module (FIGS. 2, 3).

If measurements are denoted, respectively, as $Z_-$ and $Z_+$, then the controller microprocessor calculates a more accurate value as an average value of both measurements obtained:

$$Z = (Z_- + Z_+)/2 \quad (5)$$

Measurement of Time Constant τ

Figure 4:
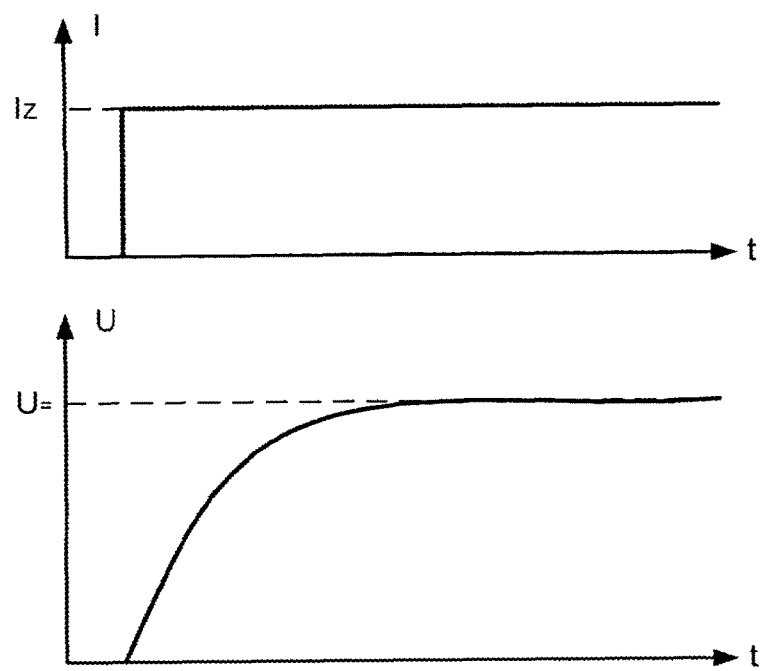
FIG. 4 shows a change in a stationary voltage on a thermoelectric module when direct current is passed.

After a stationary level of voltage drop is achieved (FIG. 4) when a measurement current of one of the set polarities passes through a TEM (FIG. 2) and after a thermoelectric Q Z is measured, the measurement current is switched OFF automatically, and the measurement path corresponds to the position shown in FIG. 1, and the controller measures time in which the voltage drop on the TEM is decreased to the value of 0.37 of the $U_\alpha$ value measured earlier (FIG. 5).

This time represents the time constant τ of the thermoelectric module. In order to improve accuracy in the same way as in the case of determining a thermoelectric Q (4), a time constant value is measured when measurement current of both polarities is passed.

If measurements are denoted, respectively, as $\tau_-$ and $\tau_+$, then the controller microprocessor calculates a more accurate value as an average value of both measurements obtained:

$$\tau = (\tau_- + \tau_+)/2 \quad (6)$$

Diagnosis of Thermoelectric Module Operability

The three parameters R, Z, τ, as measured with the use of the claimed measurement path, in combination characterize TEM operability as compared to earlier obtained measurements or to values measured before the first operation of the TEM. The diagnostic matrix of TEM defects is shown in Table 1.

TABLE 1

| Defect | R | Z | τ |
|---|---|---|---|
| 1) TEM damage | ∞ | — | — |
| 2) TEM degradation in the operation process | ↑ | ↓ | ↑ or ↓ |
| 3) Defect in the TEM wiring is present in the instrument housing | ~const | ↑ | ↓* |
| 4) Defect in the wiring of a cooled object on the TEM | ~const | ~const | ↓ |

*when fully detached from the housing~becomes two times less than the initial value Note:
Up- or down-arrow in Table 1 means an increase or decrease in the parameter, respectively.

The implementation of the algorithm of diagnosing for the three criteria (R, Z, τ) in a thermoelectric controller enables both to establish that a thermoelectric module is operable, and determine reasons causing degradation in operability and reliability of thermoelectric cooling structures.

So, in contrast to the monitoring of current and voltage in the power supply circuit of a thermoelectric module, as it is usually done by conventional controllers, and due to the development of the claimed, rather simple structure of the temperature controller measurement path comprising a DC source (may be included into the existing structures of temperature controllers) and a measuring circuit with four controllable switches it becomes possible to improve the testing criteria (parameters) as well as provide for detection of failures and reasons thereof in a TEM at early stages outside the TEM operation process as well as during intervals between operation periods. Moreover, the claimed measurement path enables to identify defective articles of manufacture at the stage of their production and commissioning.

INDUSTRIAL APPLICABILITY

The claimed measurement path of a temperature controller for a thermoelectric module may be most successfully used in structures comprising thermoelectric modules (TEMs) serving as cooling or heating elements intended for cooling, heating and thermally stabilizing various devices.

What is claimed is:

1. A measurement system for a thermoelectric module, comprising:
   a temperature controller;
   a DC source to provide first and second test signals;
   a measuring circuit made of two wires; and
   first, second, third, and fourth controllable switches being switched ON/OFF by the temperature controller, the first and second controllable switches being connectable to the DC source and the third and fourth controllable switches being grounded to allow the DC source to feed the first and second test signals to the two wires,
   wherein a first wire of the two wires is connected between the first and third controllable switches and a second wire of the two wires is connected between the second and fourth controllable switches,
   wherein the temperature controller allows the DC source to feed the first test signal to the first and second wires in order to measure a resistance of the thermoelectric module by:
      turning the first controllable switch ON to connect the first wire to the DC source,
      turning the second controllable switch OFF to disconnect the second wire from the DC source,
      turning the third controllable switch OFF to disconnect the first wire from the ground, and
      turning the fourth controllable switch ON to connect the second wire to the ground,
   wherein the temperature controller allows the DC source to feed the second test signal to the first and second wires in order to measure a first thermoelectric Q and a first time constant of the thermoelectric module by:
      turning the first controllable switch OFF to disconnect the first wire from the DC source,
      turning the second controllable switch ON to connect the second wire to the DC source,
      turning the third controllable switch ON to connect the first wire to the ground, and
      turning the fourth controllable switch OFF to disconnect the second wire from the ground, and
   wherein the first and second wires are connected to the thermoelectric module to transmit measurements to the temperature controller.

2. The measurement system according to claim 1, wherein the temperature controller measures a temperature of the thermoelectric module by turning the first, second, third, fourth controllable switches OFF.

3. The measurement system according to claim 1, wherein the temperature controller turns the first, second, third, and fourth controllable switches ON and OFF according to a set switching rate to measure the resistance.

4. The measurement system according to claim 1, wherein the temperature controller measures a second thermoelectric Q and a second time constant of the thermoelectric module by turning the first and fourth controllable switches ON and the second and third controllable switches OFF, and
   wherein the temperature controller averages the first and second thermoelectric Qs and the first and second time constants.

5. A measurement system for a thermoelectric module, comprising:
   a temperature controller;
   a DC source to provide first and second test signals;
   a measuring circuit made of two wires; and
   first, second, third, and fourth controllable switches being switched ON/OFF by the temperature controller, the first and second controllable switches being connectable to the DC source and the third and fourth controllable switches being grounded to allow the DC source to feed the first and second test signals to the two wires,
   wherein a first wire of the two wires is connected between the first and third controllable switches and a second wire of the two wires is connected between the second and fourth controllable switches,
   wherein the temperature controller allows the DC source to feed the first test signal to the first and second wires in order to measure a resistance of the thermoelectric module by:
      turning the first controllable switch ON to connect the first wire to the DC source,
      turning the second controllable switch OFF to disconnect the second wire from the DC source,
      turning the third controllable switch OFF to disconnect the first wire from the ground, and
      turning the fourth controllable switch ON to connect the second wire to the ground.

6. The measurement system according to claim 5, wherein the temperature controller measures a temperature of the thermoelectric module by turning the first, second, third, fourth controllable switches OFF.

7. The measurement system according to claim 5, wherein the temperature controller turns the first, second, third, and fourth controllable switches ON and OFF according to a set switching rate to measure the resistance.

8. A measurement system for a thermoelectric module, comprising:
   a temperature controller;
   a DC source to provide first and second test signals;
   a measuring circuit made of two wires; and
   first, second, third, and fourth controllable switches being switched ON/OFF by the temperature controller, the first and second controllable switches being connectable to the DC source and the third and fourth controllable switches being grounded to allow the DC source to feed the first and second test signals to the two wires,
   wherein a first wire of the two wires is connected between the first and third controllable switches and a second wire of the two wires is connected between the second and fourth controllable switches,
   wherein the temperature controller allows the DC source to feed the second test signal to the first and second wires in order to measure a first thermoelectric Q and a first time constant of the thermoelectric module by:

turning the first controllable switch OFF to disconnect the first wire from the DC source, turning the second controllable switch ON to connect the second wire to the DC source, turning the third controllable switch ON to connect the first wire to the ground, and turning the fourth controllable switch OFF to disconnect the second wire from the ground.

9. The measurement system according to claim 8, wherein the temperature controller measures a temperature of the thermoelectric module by turning OFF the first, second, third, fourth controllable switches.

10. The measurement system according to claim 8, wherein the temperature controller measures a second thermoelectric Q and a second time constant of the thermoelectric module by turning the first and fourth controllable switches ON and the second and third controllable switches OFF, and wherein the temperature controller averages the first and second thermoelectric Qs and the first and second time constants.

\* \* \* \* \*